US012799509B2

(12) United States Patent
Liao et al.

(10) Patent No.: US 12,799,509 B2
(45) **Date of Patent: *Nov. 17, 2026**

(54) METHOD FOR PRODUCING PHOSPHATIDYLETHANOLAMINE WITH USE OF CARBON SOURCE

(71) Applicant: NAN YA PLASTICS CORPORATION, Taipei (TW)

(72) Inventors: Te-Chao Liao, Taipei (TW); Jung-Jen Chuang, Taipei (TW); Yi-Cheng Li, Taipei (TW); Tzu-Huan Wong, Hualien County (TW); Liang-Jung Chien, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 266 days.

This patent is subject to a terminal disclaimer.

(21) Appl. No.: 18/632,432

(22) Filed: Apr. 11, 2024

(65) Prior Publication Data

US 2025/0215466 A1 Jul. 3, 2025

(30) Foreign Application Priority Data

Dec. 27, 2023 (TW) ................................ 112150953

(51) Int. Cl.
*C12P 13/04* (2006.01)
*C12N 15/87* (2006.01)
*C12P 13/06* (2006.01)

(52) U.S. Cl.
CPC .............. *C12P 13/04* (2013.01); *C12N 15/87* (2013.01); *C12P 13/06* (2013.01)

(58) Field of Classification Search
CPC ........... C12P 13/04; C12P 13/06; C12N 15/87
See application file for complete search history.

(56) References Cited

FOREIGN PATENT DOCUMENTS

| | | |
|---|---|---|
| JP | 2011527566 A | 11/2011 |
| WO | WO2009111513 A1 | 9/2009 |

OTHER PUBLICATIONS

Colman, Brian, and Eric G Norman. "Serine Synthesis in Cyanobacteria by a Nonphotorespiratory Pathway." Physiologia plantarum 100.1 (1997): 133-136. Web. (Year: 1997).*

León, Rosa, Aurora Galván, and Emilio Fernández. Transgenic Microalgae as Green Cell Factories. "Chapter 2: Transformation of Cyanobacteria." 1st ed. 2007. New York, NY: Springer New York, 2007. Web. pp. 12-22. (Year: 2007).*

Almeida, Daniela Volcan et al. "Improved Genetic Transformation of Synechococcus Elongatus PCC 7942 Using Linear DNA Fragments in Association with a DNase Inhibitor." Biotechnology Research and Innovation 1.1 (2017): 123-128. Web. (Year: 2017).*

Yang, Yiling et al. "Phototaxis in a Wild Isolate of the Cyanobacterium Synechococcus Elongatus." Proceedings of the National Academy of Sciences—PNAS 115.52 (2018): E12378-E12387. Web. (Year: 2018).*

Watanabe, Yasunori, Yasuo Watanabe, and Seiya Watanabe. "Structural Basis for Phosphatidylethanolamine Biosynthesis by Bacterial Phosphatidylserine Decarboxylase." Structure (London) 28.7 (2020): 799-809.e5. Web. (Year: 2020).*

Samson, C.A., Whitford, W., Snell, R.G et al. Contaminating DNA in human saliva alters the detection of variants from whole genome sequencing. Sci Rep 10, 19255 (2020). https://doi.org/10.1038/s41598-020-76022-4 (Year: 2020).*

Velmurugan, Rajendran, and Aran Incharoensakdi. "Metabolic Transformation of Cyanobacteria for Biofuel Production." Chemosphere (Oxford) 299 (2022): n. pag. Web. (Year: 2022).*

Arora H, Culler MD, Decker EA. Production of a High-Phosphatidylserine Lecithin That Synergistically Inhibits Lipid Oxidation with α-Tocopherol in Oil-in-Water Emulsions. Foods. Mar. 30, 2022;11(7):1014. doi: 10.3390/foods11071014. PMID: 35407101; PMCID: PMC8997968. (Year: 2022).*

Adomako, Marie et al. "Comparative Genomics of Synechococcus Elongatus Explains the Phenotypic Diversity of the Strains." Ed. by Caroline S. Harwood. mBio 13.3 (2022): e0086222. Web. (Year: 2022).*

(Continued)

*Primary Examiner* — Robert J Yamasaki
*Assistant Examiner* — Trevor Kane
(74) *Attorney, Agent, or Firm* — Li & Cai Intellectual Property (USA) Office

(57) ABSTRACT

A method for producing phosphatidylethanolamine with use of a carbon source includes: cultivating modified cyanobacteria, in which the modified cyanobacteria are cultivated in a liquid medium; undergoing a photo-fermentation process, in which the carbon source is provided to the modified cyanobacteria, so that the modified cyanobacteria convert the carbon source into serine; undergoing a filtration process, in which the liquid medium is filtered for separating the modified cyanobacteria, so as to obtain the filtered liquid medium; synthesizing the phosphatidylethanolamine, in which the filtered liquid medium and the serine are mixed with a lecithin and a phospholipase in a photoreactor, so as to obtain a phosphatidylethanolamine mixture; and undergoing an oil-water separation process, in which the phosphatidylethanolamine mixture is placed in an oil water separator and left to rest for a predetermined period of time, and the phosphatidylethanolamine is obtained from an upper layer of the phosphatidylethanolamine mixture.

12 Claims, 4 Drawing Sheets

Specification includes a Sequence Listing.

(56) References Cited

OTHER PUBLICATIONS

Lai Shujuan, Zhang Yun, Liu Shuwen, Liang Yong, Shang Xiuling, Chai Xin, Wen Tingyi, "Metabolic engineering and flux analysis of Corynebacterium glutamicum for L-serine production", Science China. Life sciences, vol. 55, No. 4, Springer, Apr. 2012(Apr. 2012), pp. 283-290.
Hai Juan Hou, Jin Song Gong, Yu Xiu Dong, Jiufu Qin, Heng Li, Hui Li, Zhen Ming Lu, Xiao Mei Zhang, Zheng Hong Xu, Jin Song Shi, "Phospholipase D engineering for improving the biocatalytic synthesis of phosphatidylserine", Bioprocess and Biosystems Engineering, vol. 42, Springer, Apr. 16, 2019(Apr. 16, 2019), pp. 1185-1194.

* cited by examiner

SEQUENCE LISTING

```
Sequence total quantity: 3
SEQ ID NO: 1           moltype = DNA  length = 1590
FEATURE                Location/Qualifiers
source                 1..1590
                       mol_type = genomic DNA
                       organism = Synechococcus elongatus
SEQUENCE: 1
atgcccaagg tcttggtgtc cgatccaatc gatcaggttg gtcttgatat cctctcgcaa  60
gtggcccaag tggatgtcaa aaccggcctg agtcctagtg agctagcgca aatcataggt  120
gaatatgacg ccctgatgct gcgcagcggg acacgtgtca cggccgaagt gatcgaagcc  180
ggccaaaaac tgcgtattat tggtcgggct ggggttggtg ttgacaatgt tgatgtcccg  240
gcggctaccc gccggggaat tgtggtcgtc aatagcccag aaggcaatac tatcgccgcg  300
gcagagcaca cactcgcaat gatgttgtcg ctgagccgcc acattccgga tgccaatgct  360
tccactaaga gtggtggctg ggatcgcaag tcttttgtcg gcactgaggt ctacaaaaaa  420
accctggggg ttgttggtct tggcaaaatc ggaagccacg tcgcgacggt cgcgaaggcg  480
atgggcatga aactcctggc ctacgacccc tttatttcag cagaacgagc ggaacagatt  540
ggggcccggt tggtcgagtt ggatattctc tttcaggaag cagactacat cacgctgcat  600
attcccaaaa cccccgaaac cgccaacctg atcaatgctg aaaccctagc caagatgaag  660
cccaccactc gcattatcaa ctgcgcccgt ggaggggtca tcaacgaaca agcacttgcg  720
gatgcgatcg ctgctggcaa aatcggcggt gcggccctgg atgtttacga tcaagagccc  780
ctccaggctg attcaccgct gcgagcactg ggtaagaacc tgatcttgac gccccatcta  840
ggtgcctcca caaccgaggc acaggtcaac gtcgcagtag acgtagcgga gcagattcgg  900
gacgtcctcc tgggcctccc agcccggagt gccgtgaaca tccctgggct ctatcctgat  960
attttggaaa agctgcggcc gtatctgcag ttggcggaaa ctctgggcaa cctccttagt  1020
caagtcgcgg gcggccgcct cgagcaactc acggttcgat tgcaaggcga gttggctgcc  1080
cagcaatctc agccgatcgt ggtggctgct ttaaaaggcc tattgaccca agcattacga  1140
gaacgtgtta actatgtcaa tgctatgatc gaggccaaag agcgcggaat tcgcatcatc  1200
gaaacacgcg atgagagcgt gcgcgatgac tatgccgggg ggtccttgca gctggttgcc  1260
acgggcagca atggtgaaca tcgtgtgatg ggcgctctgt tgggcgatgg cgagattcgg  1320
attaccaatg tggacgaatt ccctgtgaac gtcccgccca gccgatacat gctgttcacg  1380
cggcaccgcg acatgccggg catcattgga aaaattgggt cgctcttggg ttctttcaac  1440
gtgaatattg cctcgatgca ggttggacgc cgcattgtgc gcggtgacgc ggtgatggtg  1500
ctgtcgctcg atgatccgtt accagaagga atcctagcgg aaattacgaa ggtggctggc  1560
atcagcgatg cttacaccgt tgtgctctaa                                   1590

SEQ ID NO: 2           moltype = DNA  length = 1338
FEATURE                Location/Qualifiers
source                 1..1338
                       mol_type = genomic DNA
                       organism = Synechococcus elongatus
SEQUENCE: 2
atggcaacac gtgtcgtctt agtgcgtcat gggcaaagca gctacaacgc cgctggtcgg  60
atccaaggac gttgcgataa ctcgcaactg actgatcgag gcgcagcgga cgcagtcaaa  120
gttgcagctg cactgaatgg cattcccttc gctgctgcct actgctcacc actgcagcga  180
gccaaacgga cggcagaaat catcattgag cagatcgaaa cgccgccagc tttggcggtg  240
agcgatggcc ttctcgaagt cgacctgccg ctgtgggagg gcctcagtcg cgaagaagtg  300
cgctctcagt acgccgaact ctatcgccag tggcacgaag ccccccatga gctagtcctg  360
accgtgccgg acggtcaagg tggcagccgc gagcatgccc ctgttttggc tctgtttgag  420
caagcgcggc agttttggaa ggatttgttg gaacggcatc gcgatcaaac tgtactactg  480
gttgcccaca acgggattct gcgctcactg atcgcgacgg cattgggcgt tgatcctagc  540
gcctatcaag tgatccgaca atctaactgc gggatcagtg tgctcaactt cgcagatgga  600
accaatcagc cggcccagct ggaatgtcta aatctaaccg caccgcttgg cgatgccctc  660
cctgatcgcg gcgcttcgtc gggcgtccga cttctgctgg ttcgccatgg tgaaaccgac  720
tggaatcgcc aaaaacgatt ccaagggcaa atcgatattc cgctgaatga caacggtagg  780
gctcaggcgc gtagtgcggc cgaattttg gcgcccattc agattgactt tgcggtctcc  840
```

-continued

```
tcgccgatgg cgcggccgaa ggaaacggct gagctgattt tggagcgcca ccccaattgt  900
gaactgtcgg tggacgatcg cctccaagaa attggtcacg gcctctggga gggaaagctc  960
gaggaagaga tcgcagcgga attcggcgaa ttgttacagc tctggaaaga tcagcccgaa  1020
caggtgcaga tgcccgaggg ggagaacctg caagaggttt gggatcgcag cgtcgcggct  1080
tgggaagcga tcgtcgccaa tgccccagaa ggcagtaccg gcttagtggt cgctcacgat  1140
gcggtcaaca aagtgattct atgccacgtc ttgggcttgt cccccgccga catttggagc  1200
atcaagcagg gcaacggggc tgttacagtg gttgactatc ccaagcggct cgattcccgt  1260
ccagtactcc aagccatgaa tctgactctg catctcgatg gtgccgtgtt ggatcgcacc  1320
gccgcgggtg ctctttaa                                                1338

SEQ ID NO: 3            moltype = DNA  length = 1080
FEATURE                 Location/Qualifiers
source                  1..1080
                        mol_type = genomic DNA
                        organism = Synechococcus elongatus
SEQUENCE: 3
atgatgggca atcgcgtata caacttcaac gcaggacctt ctgcgatgcc gctgcccgtg  60
ttagaggaaa ttcagcagga gtttctagac tttaatcaca cgggcatgag catcgtggaa  120
atcagccatc gatcggatgc atatcaaaag atgcaggatg aaacgattgc gctccttcat  180
aagttattga atattcccga cgagtacggc attaccttca tgcaaggcgg tggttcgatg  240
cagttcctga tgcatggcgc taattttttg aagcaccgcg gggctacat caatactggt  300
gtctggagta aaaaagccaa agagggtgcg gctttttatg gcgatgtcta cgacgttgct  360
acgagtgagg gcgaaggttt tcggcggatt ccgggcccag aggaattcga tctgctgcct  420
gataccgact acgtctatct gaccagcaac aacactattc acggcacaca gtggcaagcc  480
ttcccccaca tcgatctccc gctaatatgc gatatgtcga gtgattttct ttcgcggcct  540
gtggatgtga agaactttga cttcatctat gctgggattc aaaaaaatgt tggaccagcg  600
ggggcagtga ttggtatcgc aaagcattca tacctggaaa cagcccgtca agacctgccg  660
atcatgctgc agtacaaaac cttttttgat cacgacagta cttataacac gccgcccgtt  720
ttttgcatct acttcgtcaa caaggtgttg cactggctcg atgagcgagg ggggctcaag  780
gagactgagc ggatcaacaa agaaaaggcg gcgtttgtct acgatgcgat cgatgccagc  840
gatggcttct atcgccccca tgccgccaag gattcacgca gcttgatgaa catcaccttc  900
aatctggtga cgccagaact cgagaaagaa tttgtttccc gtgcagccga agaaaaactg  960
attggtctca aaggtcatcg ttctattggc ggctgtcgcg cttccaccta taatgctgtc  1020
accaaagaag cctgtgaacg cttggccgac tttatgcacc gcttccgcaa agttcattaa  1080
```

METHOD FOR PRODUCING PHOSPHATIDYLETHANOLAMINE WITH USE OF CARBON SOURCE

CROSS-REFERENCE TO RELATED PATENT APPLICATION

This application claims the benefit of priority to Taiwan Patent Application No. 112150953, filed on Dec. 27, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for producing phosphatidylethanolamine, and more particularly to a method for producing phosphatidylethanolamine with use of a carbon source.

BACKGROUND OF THE DISCLOSURE

Cyanobacteria are autotrophs that can synthesize the required nutrients by photosynthesis. Since the cyanobacteria have the ability to fix carbon dioxide into metabolites, the cyanobacteria are conventionally applied to production of alcohols and organic acids (e.g., ethanol, butanol, 2,3-butanediol, succinic acid, lactic acid, and isopropylene), so as to reduce the greenhouse effect and damages to the environment. However, the cyanobacteria lack the ability to convert a carbon source into serine, and thus cannot be applied to production of the serine in the conventional technology.

Phosphatidylethanolamine (PE) is the main phospholipid of a soy lecithin, and its content in the soy lecithin is only next to phosphatidylcholine (PC). As a phospholipid that is present in the human brain, the phosphatidylethanolamine is also a component of cell membranes of nerve cells. Generally, the phosphatidylethanolamine is considered to be capable of facilitating conduction of electrical impulses, thereby promoting activity of neurotransmitters involved in learning, memory, emotions, etc. Hence, the phosphatidylethanolamine is used as a dietary supplement for improving physiological functions. In the conventional technology, the phosphatidylethanolamine is mainly obtained by extraction and purification of lecithins from soybeans. There is only about 0.5% to 3% of the phosphatidylethanolamine in the lecithins from the soybeans, so that sources of the phosphatidylethanolamine are rare.

Therefore, how to expand the sources for obtaining the phosphatidylethanolamine through development of a new method for producing the phosphatidylethanolamine has become one of the important issues to be solved in the related art.

SUMMARY OF THE DISCLOSURE

In response to the above-referenced technical inadequacy, the present disclosure provides a method for producing phosphatidylethanolamine with use of a carbon source.

In order to solve the above-mentioned problem, one of the technical aspects adopted by the present disclosure is to provide a method for producing phosphatidylethanolamine with use of a carbon source, which includes: cultivating modified cyanobacteria, in which the modified cyanobacteria are cultivated in a liquid medium; undergoing a photo-fermentation process, in which the carbon source is provided to the modified cyanobacteria, so that the modified cyanobacteria convert the carbon source into serine; undergoing a filtration process, in which the liquid medium is filtered for separating the modified cyanobacteria, so as to obtain the filtered liquid medium; synthesizing the phosphatidylethanolamine, in which the filtered liquid medium and the serine are mixed with a lecithin and a phospholipase in a photoreactor, so as to obtain a phosphatidylethanolamine mixture; and undergoing an oil-water separation process, in which the phosphatidylethanolamine mixture is placed in an oil water separator and left to rest for a predetermined period of time, and the phosphatidylethanolamine n an upper layer of the phosphatidylethanolamine mixture. The modified cyanobacteria include gene sequences of SEQ ID NO: 1, SEQ ID NO: 2, and SEQ ID NO: 3.

In one of the possible or preferred embodiments, the modified cyanobacteria are obtained by processes of: synthesizing a DNA sequence; implanting the DNA sequence into a plasmid; and implanting the plasmid into cyanobacteria through an electroporation treatment, so as to obtain the modified cyanobacteria.

In one of the possible or preferred embodiments, the electroporation treatment is to process for 2 msec to 10 msec at a voltage of between 0.5 kV and 1.5 kV.

In one of the possible or preferred embodiments, the electroporation treatment further includes adding polyethylene glycol having a concentration of between 0.5% and 2%.

In one of the possible or preferred embodiments, the liquid medium includes 25 mM to 50 mM of sodium bicarbonate.

In one of the possible or preferred embodiments, the cyanobacteria are *Synechococcus elongatus*.

In one of the possible or preferred embodiments, the phospholipase is a magnetic catalyst.

In one of the possible or preferred embodiments, a temperature for the photo-fermentation process ranges between 30° C. and 41° C.

In one of the possible or preferred embodiments, the modified cyanobacteria are capable of producing 3-phosphoglycerate dehydrogenase, phosphoserine phosphatase, and phosphoserine aminotransferase.

In one of the possible or preferred embodiments, the carbon source is carbon dioxide, glucose, sucrose, fructose, or galactose.

In order to solve the above-mentioned problem, another one of the technical aspects adopted by the present disclosure is to provide a method for producing phosphatidylethanolamine with use of a carbon source, which includes: undergoing a photo-fermentation process, in which modified cyanobacteria are used to produce serine; synthesizing the phosphatidylethanolamine, in which the serine is mixed with a lecithin and a phospholipase in a photoreactor, so as to obtain a phosphatidylethanolamine mixture; undergoing a filtration process, in which a filtrate is obtained by passing the phosphatidylethanolamine mixture through a membrane filter; and undergoing an oil-water separation process, in which the filtrate is placed in an oil water separator and left to rest for a predetermined period of time, and the phosphatidylethanolamine is obtained from an upper layer of the filtrate.

In one of the possible or preferred embodiments, the modified cyanobacteria include gene sequences of SEQ ID NO: 1, SEQ ID NO: 2, and SEQ ID NO: 3.

In one of the possible or preferred embodiments, a weight ratio of the lecithin to the serine is 1:5.

In one of the possible or preferred embodiments, a pore size of the membrane filter is 0.45 μm.

In one of the possible or preferred embodiments, the predetermined period of time is more than 10 minutes.

Therefore, in the method for producing the phosphatidylethanolamine with use of the carbon source provided by the present disclosure, by virtue of "cultivating the modified cyanobacteria in the liquid medium, so that the modified cyanobacteria convert the carbon source into the serine" and "the modified cyanobacteria including the gene sequences of SEQ ID NO: 1, SEQ ID NO: 2, and SEQ ID NO: 3," L-serine produced from the carbon source can act as a reaction precursor for producing the phosphatidylethanolamine, and economic benefits of a waste gas treatment can be enhanced.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
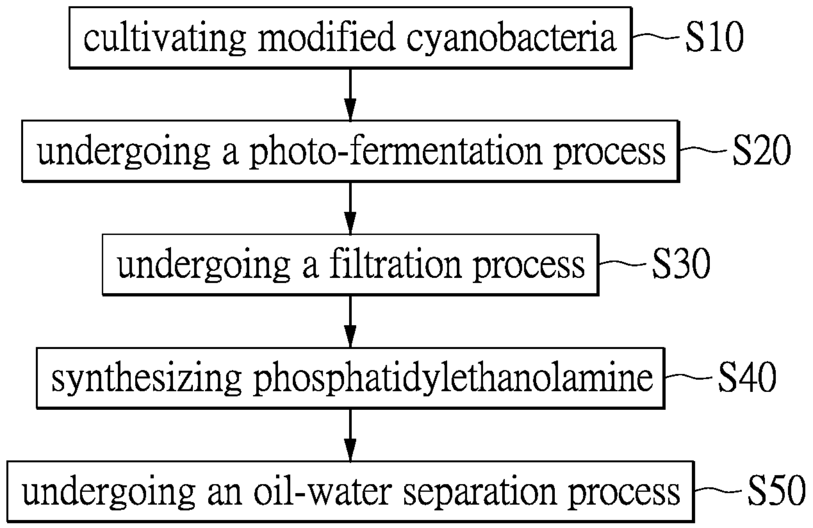
FIG. 1 is a flowchart of a method for producing phosphatidylethanolamine with use of a carbon source according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

It should be noted that, the term "or" recited in the present disclosure may include any one or a combination of relevant items listed herein according to practical requirements. Unless the context requires otherwise, the term "include", and variations such as "includes" and "including", will be understood to imply the inclusion of a stated integer or step or group of integers or steps, but not the exclusion of any other integer or step or group of integers or steps. In the present disclosure, the term "including" can be substituted with the term "containing" or "having".

The term "exogenous gene" recited in the present disclosure can also be referred to as "heterologous gene". The exogenous gene is not an endogenous genome that originates from a host cell or a target cell. Instead, the exogenous gene is taken from other species or cells, or from a synthetic gene or a nucleotide fragment, and is introduced into the host cell or the target cell by the genetic engineering technology.

An embodiment of the present disclosure provides a method for converting a carbon source into serine, which includes: synthesizing a DNA sequence; implanting the DNA sequence into a plasmid, so that the plasmid includes gene sequences of SEQ ID NO: 1, SEQ ID NO: 2, and SEQ ID NO: 3; implanting the plasmid into cyanobacteria through an electroporation treatment, so as to obtain modified cyanobacteria; and providing the carbon source to the modified cyanobacteria, so that the modified cyanobacteria converts the carbon source into the serine.

Figure 2:
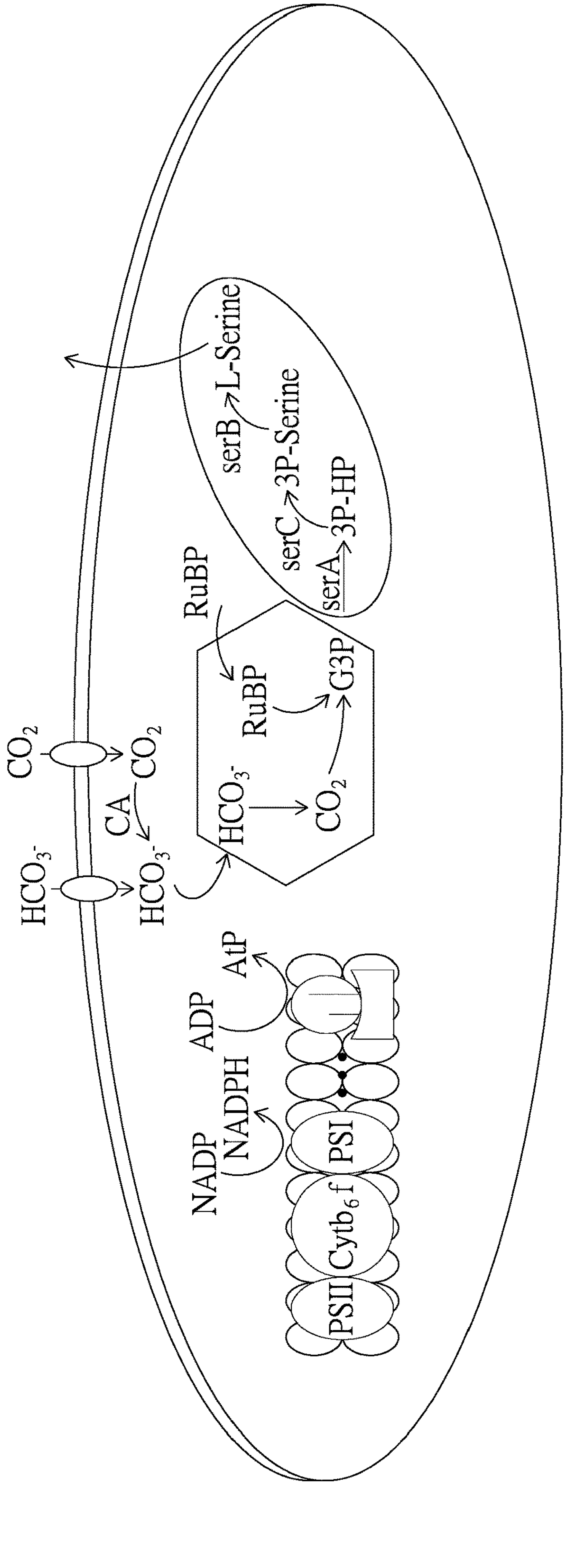
FIG. 2 is a schematic view showing a metabolic pathway of modified cyanobacteria according to the present disclosure.
Figure 3:
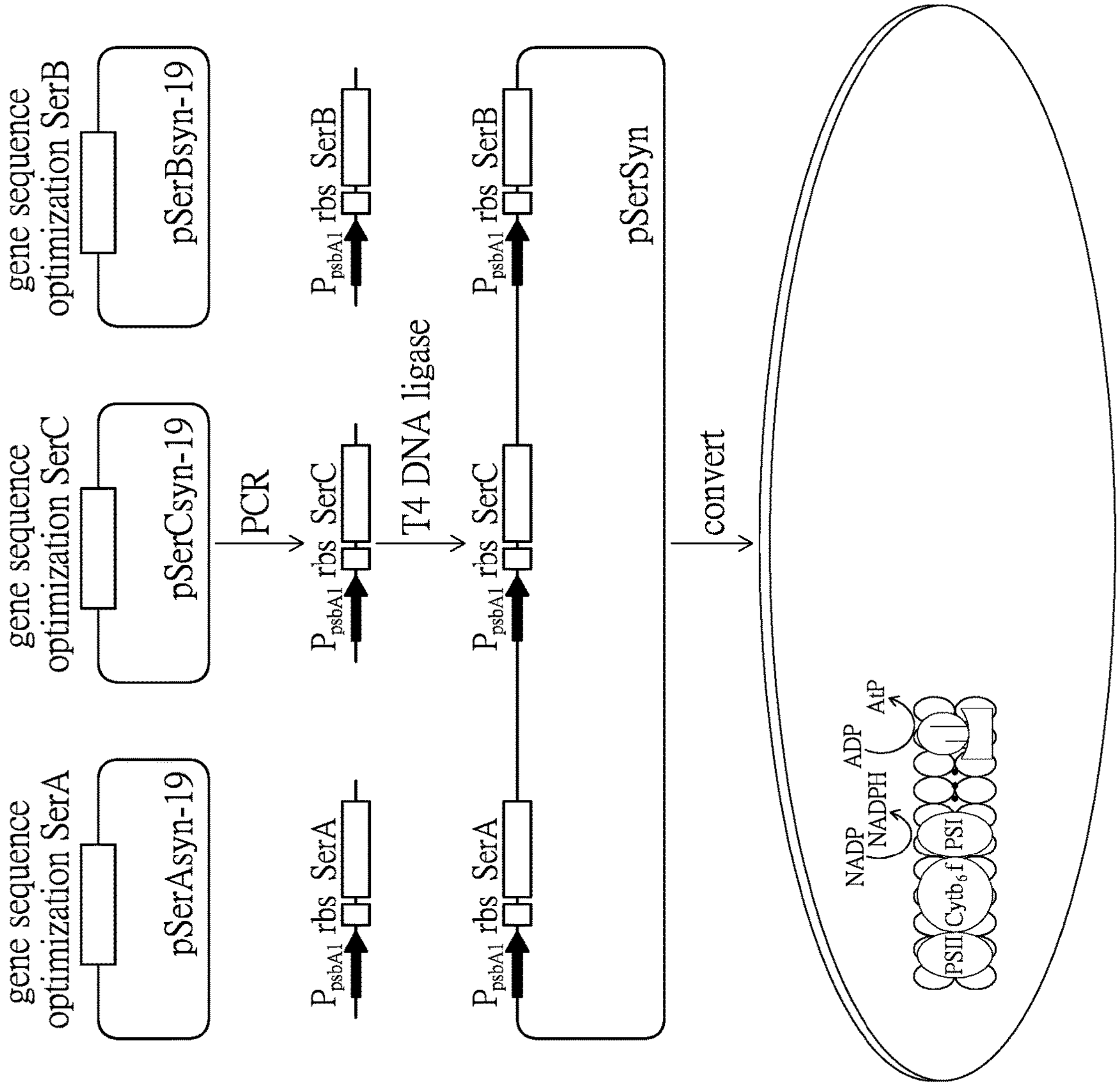
FIG. 3 is a schematic view showing construction of a plasmid according to the present disclosure.

In FIG. 2 and FIG. 3, NADP refers to nicotinamide adenine dinucleotide phosphate, NADPH refers to reduced nicotinamide adenine dinucleotide phosphate, ATP refers to adenosine triphosphate, ADP refers to adenosine diphosphate, PSII refers to photosystem II, PSI refers to photosystem I, Cytb6f refers to cytochrome b6f and is at a center of light-dependent reactions of oxygenic photosynthesis, RuBP refers to ribulose-1,5-bisphosphate, CA refers to carbonic anhydrases, and rbs refers to a ribosome binding site.

In the process of synthesizing the DNA sequence, the DNA sequence is synthesized to be suitable for genetic code recognition of the cyanobacteria, so that the cyanobacteria can recognize and produce corresponding substances. A genetic code that is suitable for genetic code recognition of *Synechococcus elongatus* PCC7942 is particularly synthesized. Furthermore, the synthesized DNA sequence can be mass produced through a polymerase chain reaction (PCR). In one embodiment of the present disclosure, PCR conditions are as follows: repeating 30 cycles of denaturing at 98° C. for 30 seconds, denaturing at 98° C. for 10 seconds, low-temperature annealing at 56° C. for 20 seconds, and polymerizing at 72° C. for 45 seconds. Afterwards, PCR amplification is carried out under conditions of polymerizing at 72° C. for 10 minutes.

A plasmid DNA is massed produced and separated from native *Escherichia coli* DH5-alpha strains. In the process of implanting the DNA sequence into the plasmid, the designed DNA sequence is inserted into an *Escherichia coli* plasmid, so as to modify *Escherichia coli* for cloning and mass production. Accordingly, a recombinant plasmid is obtained and named as pSerSyn. However, the *Escherichia coli* cannot make use of carbon dioxide ($CO_2$). Even with the designed DNA sequence, the *Escherichia coli* is still not able to convert the carbon source into the serine. Hence, the plasmid DNA that is modified and massed produced needs to be taken out and transferred to native cyanobacteria.

Specifically, pSyn_1 can act as a backbone in construction of the plasmid used in the present disclosure, and carries the gene sequences of SEQ ID NO: 1, SEQ ID NO: 2, and SEQ ID NO: 3, so as to be integrated into and expressed in a genome of the cyanobacteria by homologous exchange. Then, an antibiotic is used to filter the modified cyanobacteria that have successfully obtained SEQ ID NO: 1, SEQ ID NO: 2, and SEQ ID NO: 3 after the homologous exchange. In other words, cyanobacteria strains that are successfully modified can grow on a solid medium containing the antibiotic.

In the process of implanting the plasmid into the cyanobacteria, the cyanobacteria are cultivated in a BG-11 medium, and a growth concentration of the strain is measured based on $OD_{730}$ (optical density at 730 nm). More specifically, the plasmid is implanted into the cyanobacteria by electroporation, so as to obtain the modified cyanobacteria. In the process of electroporation, cells of the cyanobacteria are subjected to a high voltage and a low capacitance by application of an electric current within an extremely short period of time (ranging from microseconds to milliseconds), so that a potential difference in a cell membrane is formed, and changes occur to the structure of the cell membrane. As a result, the cell membrane is compressed and thinned, thereby generating numerous tiny holes. These tiny holes allow the plasmid to pass through the cell membrane and enter the cells of the cyanobacteria.

In order to achieve the optimal plasmid permeability effect, 0.5% to 2% (any concentration ranging between 0.5% and 2%) of polyethylene glycol (PEG) can be further added in this step. For example, the concentration can be 1.0% or 1.5%. Preferably, in the electroporation treatment, the cyanobacteria are processed for 2 msec to 10 msec at any voltage value ranging between 0.5 kV and 1.5 kV (e.g., 0.6 kV, 0.7 kV, 0.8 kV, 0.9 kV, 1.0 kV, 1.1 kV, 1.2 kV, 1.3 kV, and 1.4 kV). The processing time can be any millisecond within a range between 2 msec and 10 msec (e.g., 3 msec, 4 msec, 5 msec, 6 msec, 7 msec, 8 msec, and 9 msec). In the electroporation treatment, when a quantitative concentration of the native cyanobacteria is $1\times10^6$, amounts of the modified cyanobacteria strains that can be successfully obtained under different voltage and time conditions are further tested in the present disclosure (as shown in Table 1 below).

TABLE 1

(1% of PEG added in each group)

| Voltage (kV) | Time (msec) | Colony count |
|---|---|---|
| 0.5 | 2 | 6 |
| 0.5 | 5 | 12 |
| 0.5 | 10 | 21 |
| 1.0 | 2 | 19 |
| 1.0 | 5 | 36 |
| 1.0 | 10 | 11 |
| 1.5 | 2 | 17 |
| 1.5 | 5 | 32 |
| 1.5 | 10 | 8 |

From the results of Table 1, when 1% of the PEG is added in the electroporation treatment of the present disclosure, the cyanobacteria are preferably processed for 10 msec at 0.5 kV, are more preferably processed for 5 msec at 1.5 kV, and are most preferably processed for 5 msec at 1.0 kV, so as to obtain a large colony count.

Generally, the native cyanobacteria are capable of reducing carbon dioxide to glyceraldehyde 3-phosphate (G3P). However, without relevant metabolic enzymes, the native cyanobacteria cannot continue metabolizing the glyceraldehyde 3-phosphate (G3P) into L-serine. In order to process the carbon source by use of the cyanobacteria and convert the carbon source into the serine, the modified cyanobacteria are prepared in the present disclosure.

In the present disclosure, the carbon source can be an industrial waste gas (i.e., a mixture of hydrogen, acetylene, methane, hydrogen sulfide, and acetaldehyde). Specifically, the mixture can include 30 ppm to 50 ppm of the hydrogen, 150 ppm to 250 ppm of the acetylene, 100 ppm to 200 ppm of the methane, 0.1 ppm to 1 ppm of the hydrogen sulfide, and 1 ppm to 5 ppm of the acetaldehyde. For example, the industrial waste gas can be a mixture of 40 ppm of the hydrogen ($H_2$), 200 ppm of the acetylene ($C_2H_2$), 150 ppm of the methane ($CH_4$), 0.5 ppm of the hydrogen sulfide ($H_2S$), and 3 ppm of the acetaldehyde ($CH_3CHO$).

In the process of providing the carbon source to the modified cyanobacteria, the modified cyanobacteria of the present disclosure are capable of producing 3-phosphoglycerate dehydrogenase (SerA), phosphoserine phosphatase (SerB), and phosphoserine aminotransferase (SerC), so as to independently carry out reactions of Formula 1 below and convert the glyceraldehyde 3-phosphate (G3P) into the L-serine.

Formula 1

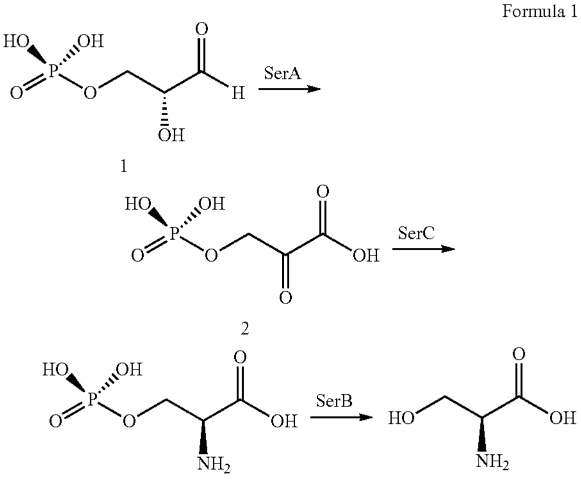

1 2 3 4

The modified cyanobacteria of the present disclosure have a plurality of exogenous genes, which include a nucleotide sequence encoded by a 3-phosphoglycerate dehydrogenase (SerA) gene, a nucleotide sequence encoded by a phosphoserine phosphatase (SerB) gene, and a nucleotide sequence encoded by a phosphoserine aminotransferase (SerC) gene. These genes can be expressed or overly expressed in the modified cyanobacteria. In other words, the modified cyanobacteria of the present disclosure have expression plasmids of SEQ ID NO: 1, SEQ ID NO: 2, and SEQ ID NO: 3.

Specifically, the modified cyanobacteria of the present disclosure still retain the property of the native cyanobacteria to convert the carbon source into the glyceraldehyde 3-phosphate (G3P). In addition, the modified cyanobacteria of the present disclosure are capable of producing the 3-phosphoglycerate dehydrogenase (SerA), so as to convert the glyceraldehyde 3-phosphate (G3P) into 3-phosphohydroxypyruvate (3P-HP). The modified cyanobacteria of the present disclosure are also capable of producing the phosphoserine aminotransferase (SerC), so as to convert the 3-phosphohydroxypyruvate (3P-HP) into 3-phosphoserine (3P-serine). The modified cyanobacteria of the present disclosure are further capable of producing the phosphoserine phosphatase (SerB), so as to convert the 3-phosphoserine (3P-serine) into the serine (especially the L-serine).

As such, the modified cyanobacteria of the present disclosure are capable of converting the carbon source into the L-serine. For example, the carbon source can be carbon dioxide, glucose, sucrose, fructose, or galactose. However, the present disclosure is not limited thereto. Preferably, the modified cyanobacteria of the present disclosure can make use of the carbon source in a carbon-containing industrial waste gas and convert the same into the L-serine. In this way, while the industrial waste gas is being processed by the modified cyanobacteria, valuable chemicals can also be obtained.

Another embodiment of the present disclosure also provides a method for converting a carbon source into serine, which at least includes using the modified cyanobacteria of the present disclosure to convert the carbon source into the serine. The modified cyanobacteria include the gene sequences of SEQ ID NO: 1, SEQ ID NO: 2, and SEQ ID NO: 3. In other words, the modified cyanobacteria have the expression plasmids of SEQ ID NO: 1, SEQ ID NO: 2, and SEQ ID NO: 3.

Accordingly, the modified cyanobacteria can convert the carbon source into the glyceraldehyde 3-phosphate (G3P). The cyanobacteria can use the sequence expressing SEQ ID NO: 1 to produce the 3-phosphoglycerate dehydrogenase (SerA), so as to convert the glyceraldehyde 3-phosphate (G3P) into the 3-phosphohydroxypyruvate (3P-HP). The cyanobacteria can also use the sequence expressing SEQ ID NO: 3 to produce the phosphoserine aminotransferase (SerC), so as to convert the 3-phosphohydroxypyruvate (3P-HP) into the 3-phosphoserine (3P-serine). The cyanobacteria can further use the sequence expressing SEQ ID NO: 2 to produce the phosphoserine phosphatase (SerB), so as to convert the 3-phosphoserine (3P-serine) into the serine.

On the other hand, the present disclosure further includes a method for producing phosphatidylethanolamine with use of a carbon source. The method includes: cultivating modified cyanobacteria (step S10); undergoing a photo-fermentation process (step S20); undergoing a filtration process (step S30); synthesizing the phosphatidylethanolamine (step S40); and undergoing an oil-water separation process (step S50). In other words, in step S10, the modified cyanobacteria are cultivated in a BG-11 medium.

Figure 4:
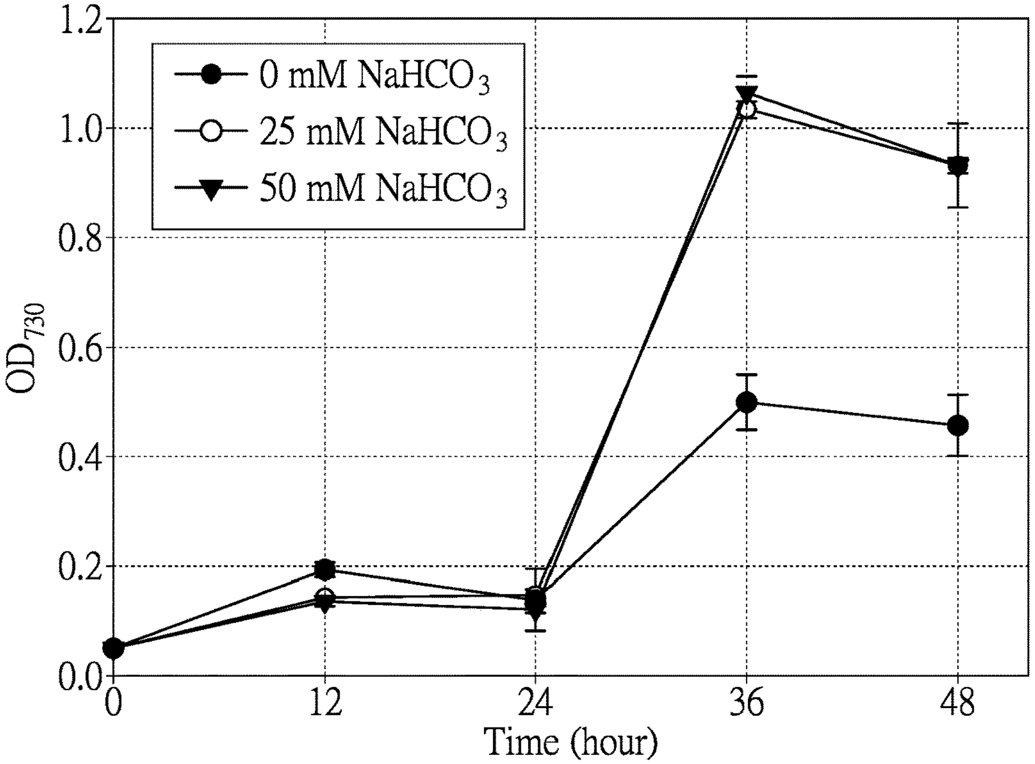
FIG. 4 is a line chart showing a relationship between a concentration of $NaHCO_3$ and a growth of cyanobacteria.

In the photo-fermentation process (step S20), the modified cyanobacteria are cultivated in an environment of a flue gas (an industrial waste gas) that contains carbon dioxide ($CO_2$). In one exemplary embodiment, sodium bicarbonate ($NaHCO_3$) is added into a culture medium of the modified cyanobacteria, so as to aid dissolution of the flue gas into the culture medium of the modified cyanobacteria. As shown in FIG. 4, a concentration of the sodium bicarbonate can range between 25 mM and 50 mM (e.g., any positive real number ranging between 25 and 50). After 24 hours of cultivation with addition of the sodium bicarbonate, a growth amount of the modified cyanobacteria is higher in an $OD_{730}$ value than that without addition of the sodium bicarbonate. This indicates that adding 25 mM to 50 mM of the sodium bicarbonate is beneficial for the growth of the modified cyanobacteria, thereby increasing a yield of L-serine.

Membrane filtration is adopted in the filtration process (step S30). For example, a liquid medium or a reaction liquid is introduced into a backwash filter, and a membrane filter of 0.45 μm is used for filtration, so as to filter out cells of the modified cyanobacteria and obtain a filtrate that contains serine or the phosphatidylethanolamine. The modified cyanobacteria that are filtered out can be recycled into a photo-fermentation reactor for reuse during the photo-fermentation process, so as to reduce the manufacturing costs.

Specifically, in one embodiment, the liquid medium can firstly be filtered for filtering out cells of cyanobacteria, and the filtered liquid medium is mixed with a lecithin and a phospholipase for the step of synthesizing the phosphatidylethanolamine. In this embodiment, a reaction in which the modified cyanobacteria convert the carbon source into the serine is prevented from interfering with a synthesis reaction of the phosphatidylethanolamine. In another embodiment, the lecithin and the phospholipase can be directly added into the liquid medium of the modified cyanobacteria for the synthesis of the phosphatidylethanolamine. Device costs can be reduced when the reaction is carried out in a one-pot manner.

Figure 5:
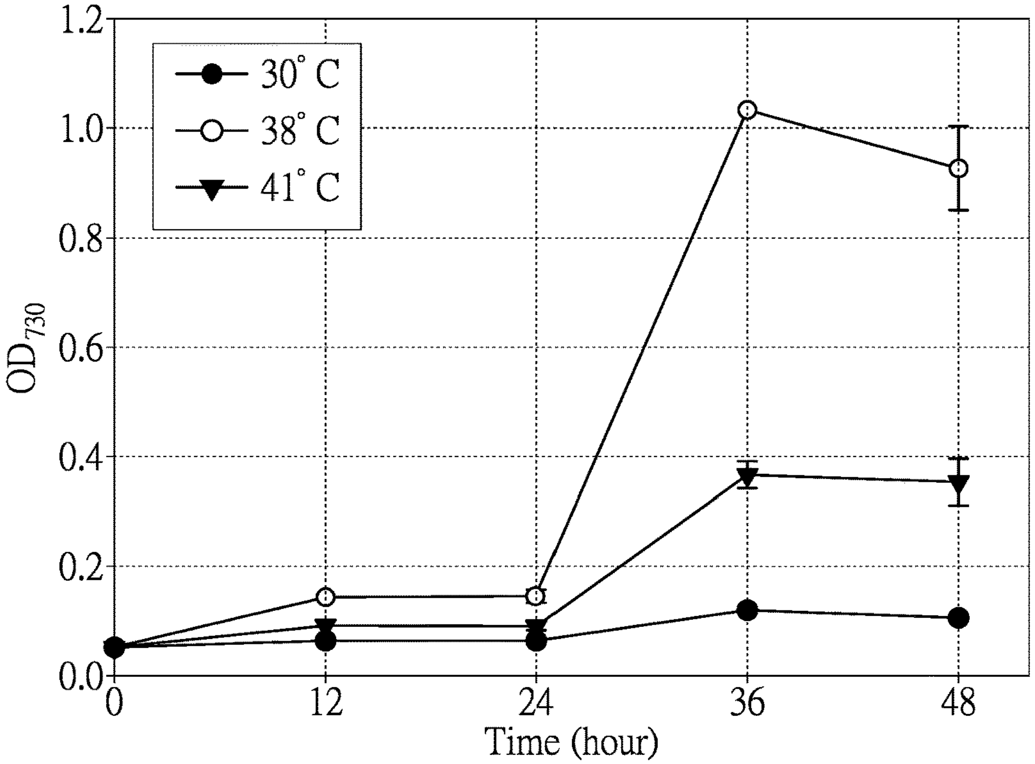
FIG. 5 is a line chart showing a relationship between a temperature of a photo-fermentation reactor and the growth of the cyanobacteria.

In the step of synthesizing the phosphatidylethanolamine (step S40), the modified cyanobacteria and the L-serine produced thereby are mixed with the lecithin and the phospholipase in a photoreactor, or the filtered liquid medium containing the L-serine (but not the cells of the modified cyanobacteria) is mixed with the lecithin and the phospholipase in the photoreactor, so as to obtain a phosphatidylethanolamine mixture. In one embodiment of the present disclosure, a temperature for the photo-fermentation process ranges between 30° C. and 41° C., such as 30° C., 31° C., 32° C., 33° C., 34° C., 35° C., 36° C., 37° C., 38° C., 39° C., 40° C., or 41° C. (any temperature ranging between 30° C. and 41° C.). It is worth mentioning that the most suitable temperature for the photo-fermentation process is 38° C., at which an optimal strain growth amount can be obtained (as shown in FIG. 5).

Furthermore, the phospholipase of the present disclosure is added in the form of a magnetic catalyst. A preparation method of the magnetic catalyst includes: (A) preparation of magnetic nanoparticles (MNP); (B) surface modification; and (C) enzyme immobilization. A detailed description thereof is provided below.

In (A) preparation of magnetic nanoparticles, 200 mL of iron (II) sulfate heptahydrate at 8.85% (w/v), 100 mL of potassium nitrate at 10.11% (w/v), and 50 mL of potassium hydroxide at 27.62% (w/v) are added into a serum bottle of 500 mL, and are stirred for 120 minutes in a water bath at 90° C. The generated magnetic nanoparticles are separated and collected by use of a magnet, and are alternately washed by deionized water of the same volume and 95% ethanol for three times. After each washing, the magnetic nanoparticles are separated and adsorbed by the magnet for about 5 minutes, and then the washing solution is removed by suction.

In (B) surface modification, after a concentration of the prepared magnetic nanoparticles is adjusted to be 10 mg/mL, 1 mL of the magnetic nanoparticles are suctioned and placed in a microcentrifuge tube. Then, the magnet is used to collect and adsorb the magnetic nanoparticles for about 5 minutes before removal of a supernatant, and 1 mL of the deionized water is used to wash the magnetic nanoparticles for three times, so as to completely remove ethanol. After each washing, the magnetic nanoparticles are collected and adsorbed by the magnet for about 5 minutes, and then the supernatant is removed. After removal of the ethanol, 500 μL of the deionized water is further added to prepare a magnetic nanoparticle (MNP) suspension.

2.5 mg of dopamine hydrochloride (DA) is weighed and placed in a small glass bottle, and 500 μL of the deionized water is added for stirring and dissolution, so as to prepare a dopamine hydrochloride (DA) solution. The MNP suspension is added into the DA solution, and 1 μL of 10N sodium hydroxide (NaOH) is further added, so that a pH value is adjusted to be 8.5 before being stirred for another 3 hours. After about 2 hours of stirring, the pH value is decreased to 7. In order for the pH value to be adjusted back to 8.5, sodium hydroxide needs to be further added. The modified DA-MNPs are collected by the magnet and washed by 1 mL of the deionized water for five times. During each washing, the DA-MNPs are separated and collected by the magnet for about 5 minutes before removal of the supernatant. After the washing is completed, the DA-MNPs are resuspended (in a volume of 1 mL) with use of the deionized water, and are treated by ultrasound for 15 minutes before being preserved under 4° C.

In (C) immobilization of phospholipase D, the DA-MNPs and a phospholipase D are mixed at different ratios in 5 mM of a phosphate buffer solution (pH 6.8), and left to rest for 5 minutes. Then, the magnet is used for adsorption for 5 minutes, so as to separate the DA-MNPs. After three times of repeated washing with ultrapure water and magnetic adsorption and separation, the DA-MNPs that have encapsulated the phospholipase D are reconstituted into the ultrapure water of the same volume for later use.

In one embodiment of the present disclosure, 1 mol of the lecithin and 0.05 wt % to 5 wt % (relative to the lecithin) of the magnetic nanoparticles are added into 1 L of the cyanobacteria/L-serine (containing 5 mol of the serine). Through catalysis of the phospholipase, a trimethylethanaminium functional group in the lecithin is replaced to produce the phosphatidylethanolamine, and specific details thereof are as shown in Formula 2 below.

Formula 2

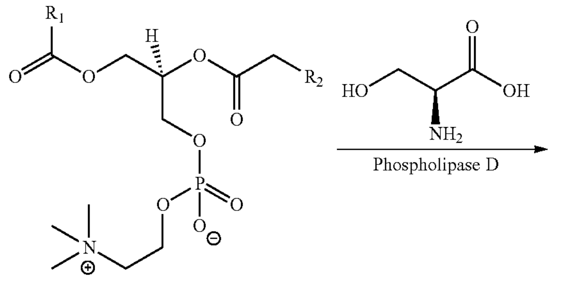

$R_1$, $R_2$ = $C_{16}$-$C_{18}$

-continued

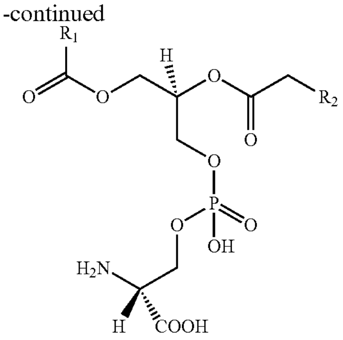

It is worth mentioning that, through adjustment of the pH value, the phosphatidylethanolamine obtained after the reaction is immiscible with water in the present disclosure. Hence, purification can be carried out via an oil-water separation system. Specifically, a pH value of the filtrate obtained by the filtration process ranges between 1 and 3.

As such, in the oil-water separation process (step S50), the filtrate is placed in an oil water separator and left to rest and separate. A partition is disposed in the oil water separator, so that an organic phase of an upper layer may overflow to a right side of the oil water separator through the partition, and an aqueous phase of a lower layer is retained in the oil water separator, thereby achieving the purpose of oil-water separation and obtaining the phosphatidylethanolamine of the organic phase. In addition, the separated aqueous phase can be recycled and reused in a $NaHCO_3$ aqueous solution, thereby reducing the manufacturing costs. In one embodiment of the present disclosure, the time for resting and separation is more than 10 minutes.

In one embodiment of the present disclosure, the modified cyanobacteria of the present disclosure are cultivated for 60 hours in an environment of 38° C., 3% of $CO_2$, and 25 mM of $NaHCO_3$, and as high as 2.78 g/L of the L-serine can be produced. More specifically, a soy lecithin and the L-serine (at a ratio of 1:5) are reacted in an environment of 10 mM of calcium ions ($Ca^{2+}$) and 45° C. for 12 hours, and 1.86 g/L of the phosphatidylethanolamine can be produced with a conversion rate of about 83.2%. That is, when a weight ratio of the soy lecithin to the L-serine is 1:5, the conversion rate of converting the serine of the modified cyanobacteria into the phosphatidylethanolamine can be increased, thereby enhancing economic benefits.

Beneficial Effects of the Embodiments

In conclusion, in the method for the producing phosphatidylethanolamine with use of the carbon source provided by the present disclosure, by virtue of "cultivating the modified cyanobacteria in the liquid medium, so that the modified cyanobacteria convert the carbon source into the serine" and "the modified cyanobacteria including the gene sequences of SEQ ID NO: 1, SEQ ID NO: 2, and SEQ ID NO: 3," the L-serine produced from the carbon source can act as a reaction precursor for producing the phosphatidylethanolamine, and the economic benefits of a waste gas treatment can be enhanced.

Furthermore, in the present disclosure, the modified cyanobacteria strains are configured to include the gene sequences of SEQ ID NO: 1, SEQ ID NO: 2, and SEQ ID NO: 3, so as to express the property of converting the carbon source into the serine. Specifically, in an environment where the carbon source is sufficient, the modified cyanobacteria of the present disclosure can produce 35.2 mg/L to 46.3 mg/L of the serine per hour. In addition, when the lecithin and the L-serine are prepared at a ratio of 1:5 and reacted in an environment of 10 mM of calcium ions ($Ca^{2+}$) and 45° C. for 12 hours, a high conversion rate (83.2%) can be achieved. In the present disclosure, the phospholipase is modified on the magnetic catalyst, so that the phospholipase can be directly put into the photo-fermentation reactor for a one-pot reaction. In this way, an operation process is simple, and recycling and reuse are achievable, thereby reducing the manufacturing costs.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

STATEMENT REGARDING SEQUENCE LISTING

This application contains a sequence listing in XML format, which has been submitted electronically and is hereby incorporated by reference in its entirety. The sequence listing, created on Jun. 17, 2024, is named 112P001831US-Sequence listing.xml and is 7,342 bytes in size.

What is claimed is:

1. A method for producing phosphatidylethanolamine with use of a carbon source, comprising:

cultivating a modified cyanobacteria capable of producing serine by photo-fermentation in a liquid medium comprising a carbon source, wherein the modified cyanobacteria encode the genes comprising of SEQ ID NOs: 1-3;

separating the cultivated modified cyanobacteria from the liquid medium by filtration to obtain a filtered liquid medium;

synthesizing phosphatidylethanolamine by adding the filtered liquid medium to a photoreactor comprising lecithin and phospholipase as to obtain a phosphatidylethanolamine mixture;

adding the phosphatidylethanolamine mixture to undergoing an oil-water separator for a predetermined period of time to separate the oil from the water; and obtaining the phosphatidylethanolamine from the oil layer;

wherein the cyanobacteria are *Synechococcus elongatus*.

2. The method according to claim 1, wherein the modified cyanobacteria are obtained by processes of:

synthesizing a DNA sequence of SEQ ID NOs: 1-3;

implanting the DNA sequence into a plasmid; and implanting the plasmid into cyanobacteria through an electroporation treatment, so as to obtain the modified cyanobacteria.

3. The method according to claim 2, wherein the electroporation treatment is to process for 2 msec to 10 msec at a voltage of between 0.5 kV and 1.5 kV.

4. The method according to claim 2, wherein the electroporation treatment further includes adding polyethylene glycol at a concentration of between 0.5% and 2%.

5. The method according to claim 1, wherein the liquid medium includes 25 mM to 50 mM of sodium bicarbonate.

6. The method according to claim 1, wherein the phospholipase is a magnetic catalyst.

7. The method according to claim 1, wherein a temperature for the photo-fermentation process ranges between 30° C. and 41° C.

8. The method according to claim 1, wherein the carbon source is carbon dioxide, glucose, sucrose, fructose, or galactose.

9. A method for producing phosphatidylethanolamine from a carbon source, comprising:

cultivating a modified cyanobacteria capable of producing serine by photo-fermentation;

synthesizing phosphatidylethanolamine by mixing the serine produced with a lecithin and a phospholipase in a photoreactor, to obtain a phosphatidylethanolamine mixture;

filtering the phosphatidylethanolamine mixture through a membrane filter to obtain a filtrate;

adding the filtrate to an oil-water separator for a predetermined period of time to separate the oil from the water; and obtaining the phosphatidylethanolamine from the oil layer;

wherein the modified cyanobacteria are *Synechococcus elongatus* including gene sequences of SEQ ID NO: 1, SEQ ID NO: 2, and SEQ ID NO: 3.

10. The method according to claim 9, wherein a weight ratio of the lecithin to the serine is 1:5.

11. The method according to claim 9, wherein a pore size of the membrane filter is 0.45 μm.

12. The method according to claim 9, wherein the predetermined period of time is more than 10 minutes.

* * * * *